(12) United States Patent
Burmaster

(10) Patent No.: US 7,078,201 B2
(45) Date of Patent: Jul. 18, 2006

(54) ETHANOL FERMENTATION USING OXIDATION REDUCTION POTENTIAL

(76) Inventor: Brian M. Burmaster, 14033 Forest Crest, Chesterfield, MO (US) 63017

( * ) Notice: Subject to any disclaimer, the term of this patent is extended or adjusted under 35 U.S.C. 154(b) by 0 days.

(21) Appl. No.: 11/291,762

(22) Filed: Nov. 30, 2005

(65) Prior Publication Data

US 2006/0115884 A1 Jun. 1, 2006

Related U.S. Application Data

(60) Provisional application No. 60/632,212, filed on Dec. 1, 2004.

(51) Int. Cl.
*C12P 7/06* (2006.01)
*C12P 7/08* (2006.01)
*C12P 7/14* (2006.01)

(52) U.S. Cl. .................. 435/161; 435/29; 435/162; 435/163

(58) Field of Classification Search ................ 435/161, 435/162, 163, 29
See application file for complete search history.

(56) References Cited

U.S. PATENT DOCUMENTS

| 3,123,475 A | 3/1964 | Wendt et al. |
| 3,384,553 A | 5/1968 | Caslavsky et al. |
| 4,046,921 A | 9/1977 | Akao et al. |
| 4,204,042 A | 5/1980 | Chelle |
| 4,346,113 A | 8/1982 | Faust et al. |
| 4,468,455 A | 8/1984 | Hopkins |
| 4,477,569 A | 10/1984 | Schneider et al. |
| 5,177,008 A | 1/1993 | Kampen |
| 5,633,165 A | 5/1997 | Swartz |
| 2005/0194311 A1* | 9/2005 | Rozich ........................ 210/614 |

OTHER PUBLICATIONS

Kansas State University David Contrain "Economies of Ethanol" Risk & Profit 2001 Conference Aug. 16-17, 2001; Slide 26.

S. Alfenore, et al. "Aeration strategy: a need for vey high ethanol performance in Saccharomcyes Cerevisiae fed-batch process" Applied Microbiology and Biotechnology 2004.

Ingledew, W.M. Chapter 5; "Alcohol Production by Saccharomyces Cerevisiae: A yeast primer" The Alcohol Textbook; 3rd Edition, Kacquies et al, Nottingham Press; 1999, pp. 49-87.

"The Role of On-line Redox Potential Measurement in Sauvigon blan Fermentation". Food Technology Biotechnology 2002 Article 40 Aleksandra Kurec,et al.

* cited by examiner

*Primary Examiner*—Herbert J. Lilling
(74) *Attorney, Agent, or Firm*—Paul M. Denk

(57) ABSTRACT

A process to improve ethanol yield, decrease fermentation time and reduce byproduct formation by monitoring and controlling oxidation reduction potential (redox) of the fermentor is disclosed.

5 Claims, 3 Drawing Sheets

DIRECT AERATION OF FERMENTOR

INDIRECT AERATION

ETHANOL FERMENTATION USING OXIDATION REDUCTION POTENTIAL

CROSS REFERENCE TO RELATED APPLICATION

This nonprovisional patent application claims priority to the provisional patent application having Ser. No. 60/632,212, which was filed on Dec. 1, 2004.

FIELD OF INVENTION

This invention discloses the monitoring and controlling of oxidation reduction potential (ORP or redox) during the fermentation process for the production of ethanol. This novel process is intended for the burgeoning fuel ethanol industry, where both measurement and control of oxidation reduction potential is not currently practiced. With tighter controls on ORP, the new ethanol process will deliver higher yields, shorter fermentation times, and decreased byproduct formation.

Ethanol has become an important fuel in today's economy and is expected to become more important in the future. Ethanol can be made from a variety of grains and sugar sources, including but not limited to corn, sorghum, wheat, barley, molasses, cane syrup, potatoes, and whey. Two major (dry mill and wet mill) processes are used to manufacture ethanol, which include some common steps, such as milling, liquefaction and fermentation. This invention will primarily focus on controlling ethanol fermentation, by measuring and controlling the oxidation reduction potential of the corn mash.

An economic study performed by Kansas State University (Coltrain, David; "Economics of Ethanol"; Risk and Profit 2001 Conference; Holiday Inn of Manhattan, Kans.; Aug. 16–17, 2001; slide 26) showed that 50% to 70% of the total production cost is attributed to the cost of grain usage. An important index of manufacturing economics is the ethanol yield, which is typically measured as gallons of anhydrous ethanol produced per bushel of grain. Under current practice, this yield ranges from 2.5 to 2.8 gallons per bushel. A yield improvement of 10% would have an enormous impact on the profitability of an industrial fuel ethanol producer.

Major yield losses are attributed to unconverted starch in the fermentor and unwanted byproduct formation. The major byproduct formed in the ethanol fermentation process is glycerol, as indicated in the article by S. Alfenore et al.; "Aeration strategy: a need for very high ethanol performance in *Saccharomyces Cerevisiae* fed-batch process"; *Applied Microbiology and Biotechnology* (2004); Volume 63; pages 537–542. Typical results are shown below in Table One:

TABLE 1

Typical Byproducts of Ethanol Fermentation

| Components | Units | Concentration |
|---|---|---|
| Ethanol | g/l | 131 |
| Glycerol | g/l | 12.2 |
| Acetate | g/l | 0.51 |
| Succinate | g/l | 0.74 |

Industrial HPLC (High Performance Liquid Chromotography) analysis of products leaving the ethanol fermentor confirms, as well, that glycerol is the major byproduct. Glycerol is soluble in water and leaves the fuel alcohol plant as Distiller's Dried Grains and Solubles (DDGS). Attempts to recover glycerol from the thin stillage stream, such as shown in U.S. Pat. No. 5,177,008 by Kampen have not been commercially successful.

Glycerol formation in fermentation by the yeast *Saccharomyces Cerivisiae* has been studied for a long time. The earliest manufacture of glycerol via fermentation was practiced during World War I by the German biochemist Carl Neuberg which enabled Germany to produce more than a thousand tonnes per month of glycerol by addition of a bi-sulfite solution to the fermenting mash.

Later biochemical studies verified that glycerol is produced by the yeast *Saccharomyces Cerivisiae* as a cellular redox balance. Strong reductants such as sulfite and bi-sulfite would encourage more production of glycerol. Other reductants, such as ammonia, would also favor glycerol formation. Some reductants that can be found in industry:

Sulfites, Bi-sulfites and Sulfur Dioxide
Ammonia
Hydrazine
Reducing gases such as hydrogen and carbon monoxide Naturally, this list does not include all reductants. However, it should be noted that ammonia is used in the ethanol industry to elevate the corn mash pH prior to liquefaction. Additionally, sulfite is used in the wet mill ethanol process for grain separation.

Substitution of ammonia with a more oxidizing caustic would raise the oxidation reduction potential (ORP) and lead to lower glycerol formation. Similarly, sulfite replacement or oxidation to sulfate would raise ORP and minimize glycerol production. Another method of increasing ORP would be to add an oxidant, such as:

Hydrogen peroxide
Ozone
Dihalides (Chlorine, Bromine, Iodine.)
Chlorine Dioxide
Potassium Permaganate
Air or oxygen sparging Glycerol formation decreased from 0.042 grams per gram of glucose to 0.010 grams per gram of glycose, when more oxidizing conditions were present under full aeration consistent with the data supplied by Alfenore et al. Raising the oxidation reduction potential also has the beneficial effect of improving the average ethanol productivity from 2.6 grams of ethanol per liter per hour to 3.3 grams of ethanol per liter per hour.

However, under these full aeration conditions, ethanol yield decreased from 0.46 grams of ethanol to 0.43 grams of ethanol for the full aeration case. This decrease in yield can be attributed to the increase in biomass (i.e. yeast) concentration or aerobic yeast respiration. It should also be noted that ORP was not measured in this study, but instead dissolved oxygen of the fermentation broth was monitored. Aqueous ammonia was also added for pH control, which will lower the ORP.

It is clear from a study of the literature that fully oxidizing conditions would not lead to optimal ethanol yields. Likewise, a strong reducing environment, such as is present with the addition of bi-sulfite, ethanol formation would be discouraged and glycerol formation would be encouraged.

It is the intent of this invention to show that an optimal level of oxidation reduction potential would increase ethanol yield, decrease glycerol formation and reduce fermentation time than the current practice.

Various prior art patents have been available to describe ethanol fermentation processes, and the like. For example, the Wendt U.S. Pat. No. 3,123,475, describes a typical sequential batch ethanol fermentation process, which is employed widely throughout the fuel alcohol industry. There is no mention of oxidation-reduction potential in this patent.

One of the more pertinent examples of prior art, specifically U.S. Pat. No. 3,384,553 used dissolved oxygen meters to monitor the yeast (*Saccharomyces Cerevisiae*) formation under aerobic (not anaerobic ethanol producing) conditions. Dissolved oxygen probes suffer from fouling and require constant calibration. Additionally, under very low oxygen concentrations this measurement is highly inaccurate and unreliable.

In U.S. Pat. No. 4,046,921, there is no mention of yeast, and certainly not, *Saccharomyces Cerevisiae*, or Oxidation Reduction Potential. The patent is directed towards cultivating microorganisms by a fluidized bed.

Chelle discloses in U.S. Pat. No. 4,204,042 a method to agitate and gasify a fermentor under aerobic conditions. There is no mention of Oxidation Reduction Potential or yeast.

In U.S. Pat. No. 4,346,113, Faust et al claim the merits of feeding an exact amount of oxygen bearing gas to the fermentor to reach the optimal production of ethanol. There is no further discussion on what is meant by the phrase "optimal production". The yeast *Saccharomyces Cerevisiae* was used in one of the examples. Dissolved oxygen concentration was measured at a low level (0–1 ppm), but no explanation was given when the dissolved oxygen was measured. It should also be noted that there is no mention of measuring or controlling oxidation reduction potential.

Hopkins in U.S. Pat. No. 4,468,455 directs our attention to an online dissolved oxygen probe with cell culture control of an aerobic micro-organism. Yeast is mentioned in the patent, but ethanol is not. Redox potential probe is cited in claim 6(c), but no values are given, measured or controlled.

In U.S. Pat. No. 4,477,569, Schneider et al discloses that fermentation of pentose by a selected yeast strain is benefited from air addition, as shown in the corresponding Table One. There is no mention of either the industrial yeast *Saccharomyces Cerevisiae* nor measuring oxidation reduction potential in the fermentation broth.

Swartz, in U.S. Pat. No. 5,633,165, discloses the use of online redox (oxidation reduction potential) measurements in a bacterial fermentation in FIGS. 27B, 28B, 29B, 30B, 31B and 32B under aerobic conditions. Ethanol producing yeast are not cited in the patent. However, it is interesting to note on some figures that the agitation rate was lowered to check the dissolved oxygen probe zero.

It should be remembered that all prior art does not explain the role that oxidation reduction potential plays in ethanol fermentation. No attempt was made in the prior art to define what constitutes the optimal redox level for ethanol yield and/or ethanol productivity. This invention is therefore truly novel and non-obvious.

SUMMARY OF THE INVENTION

In accordance with this invention, there is provided a process to monitor and control oxidation reduction potential to improve the overall ethanol yield, reduce glycerol formation, and decrease fermentation time. Optimal oxidation reduction potential will be found in the range of −200 mV to +350 mV where the yeast *Saccharomyces Cerevisiaie* is known to survive. The novel process is directed to the fuel alcohol industry, but could also be used in the distilled spirits, beer and wine-making industries, as well.

It is, therefore, the principal object of this invention to provide means for achieving oxidation reduction potential, and its control, for use in the fermentation such as the production of ethanol, whether for industrial, beverage, or for any usage and application.

Still another object of this invention is to provide a process that monitors and controls the oxidation reduction potential for the purpose of improving fermentation such as but not limited to ethanol.

Another object of this invention is to provide a process to reduce glycerol formation, thereby decreasing the fermentation time such as for the production of ethanol, but not limited to it.

These and other objects may become more apparent to those skilled in the art upon review of the summary of the invention as provided herein, and upon undertaking a study of the description of its preferred embodiment, in view of the drawings.

BRIEF DESCRIPTION OF INVENTION

Figure 1:
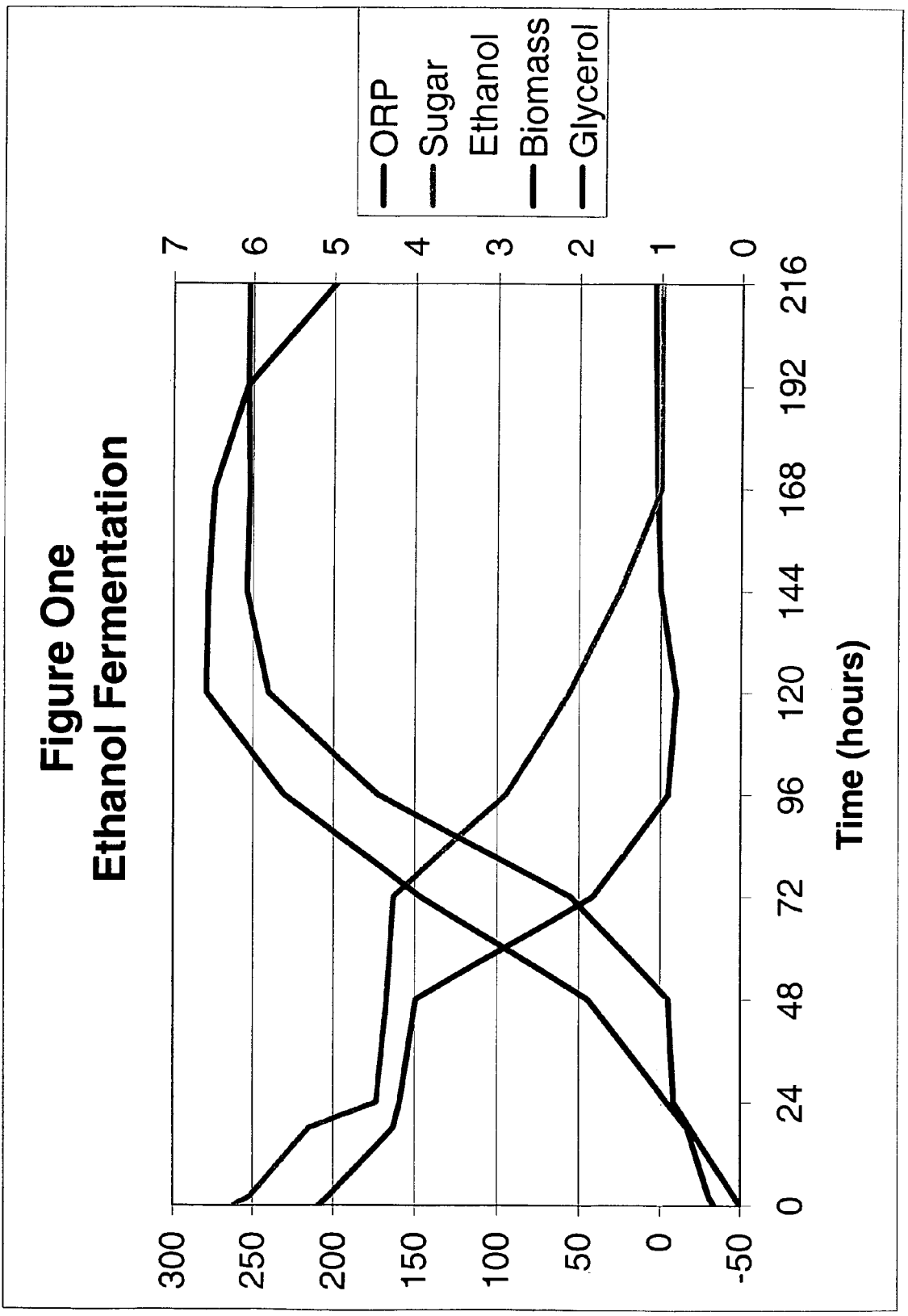
FIG. 1 provides a chart of ethanol fermentation and the typical oxidation potential curve raised during ethanol fermentation.

Oxidation reduction potential, which is typically measured in millivolts, is the tendency of a chemical species to gain or lose electrons by reaction. Oxidation is the loss of electrons by an atom, molecule or ion. When a substance is oxidized, its oxidation state is increased. Reduction is the net gain of electrons and when the substance is reduced, its oxidation state is decreased. These oxidation-reduction reactions follow the well known Nernst equation.

Oxidation reduction potential can be measured by two methods. The first method employs a titration with either a known concentration of an oxidant or reductant to an endpoint color, similar to pH titration. An example of this titration would be measuring a reductant by titrating with potassium permanganate ($KMnO_4$), which forms a deep blue-purple solution, when dissolved in water. The endpoint of the titration is established when the dark color changes to a pink solution. Another example of an ORP titration is with a soluble starch solution and potassium iodide and iodine mixture. Since there is a known concentration of reductant or oxidant, the ORP can be determined. These analytical titrations are prone to human error and are quite laborious. Additionally, as with any offline measurement, there is a delay involved.

The preferred method utilizes an online oxidation reduction potential measurement. The principle behind the ORP measurement utilizing an inert platinum or gold electrode, which due to its inherently low resistance, will give up electrons from an oxidant or accept electrons from a reductant. The ORP electrode will continue to give up or accept electrons until an electrical potential is developed which matches the oxidation reduction potential of the solution. The reference electrode used for ORP measurement is typically made from the same silver—silver chloride electrode as pH measurements. Usually, the pH electrode can measure ORP, as well, such as the Rosemount Model 389 pH/ORP sensor or the Yokogawa Model PH20 and FU20. Likewise, the transmitters are typically combination pH and ORP such as the Rosemount Model 1055 Analyzer or the Yokogawa Model PH402G pH/ORP converter.

By utilizing online measurements, the oxidation reduction potential of ethanol fermentation can be adjusted by one of these methods, but is not limited to these methods 1. Oxidant addition (such as air or oxygen sparging, peroxide etc).
2. Reductant substitution (such as ammonia with caustic)
3. Reductant elimination (such as oxidation of sulfite)

Currently, the range of the yeast *Saccharomyces Cerevisiae* activity is between −200 millivolts and +350 millivolts, according to Kukec et al. in the article entitled "The Role of On-Line Redox Potential Measurement in Sauvignon Blanc Fermentation"; *Food Technology and Biotechnology*; Volume 40 (2002); Number 1; page 50. Above +350 millivolts, oxygen acts toxically and inhibitory and below −200 millivolts, the concentration of dissolved oxygen is too low for normal life conditions of yeast. However, this range is too large for process control, and further experiments should determine the oxidation reduction potential which is optimal for ethanol yield.

Data taken at SIUE's Corn to Ethanol laboratory clearly shows that the addition of a reductant (sodium bi-sulfite) in the quantity of 0.14 grams per liter of fermentor liquid leads to the following results:

1. Higher glycerol to ethanol ratios (gm glycerol per 100 gm ethanol)
   10.36 for the corn mash without bi-sulfite
   11.42 for the corn mash with bi-sulfite
2. Lower yeast viability counts averaged during the fermentation
   468 MM per ml in the corn mash without bi-sulfite
   332 MM per ml in the corn mash with bi-sulfite
3. Higher residual starch content
   2.78 equivalence in the corn mash without bi-sulfite
   3.78 equivalence in the corn mash with bi-sulfite
4. Slower fermentation times by 5–7% with addition of bi-sulfite.

DESCRIPTION OF THE PREFERRED EMBODIMENTS

FIG. 1 shows a typical oxidation reduction potential curve during ethanol fermentation. Although the fermentation was conducted under low temperature conditions, the trends are very clear. Redox decreases from an initial positive oxidizing and aerobic (~+225 mv) value to a negative (~−100 mv) anaerobic value, as shown on the left hand scale. Meanwhile, the biomass concentration clearly increases from ~0.3 grams per liter to a maximum value of 7.2 grams per liter, as shown on the right hand scale, while the redox decreases in value. Similarly, the reducing sugar concentration decreases from 250 grams per liter to zero and parallels the oxidation reduction potential, but with a lag in time. During the same period, ethanol concentration increases from zero to a maximum of ~90 mg/liter, as shown on the left hand scale. Meanwhile, the concentration of glycerol increases from zero to 7 grams per liter, as shown on the right hand scale. It should be noted that all the measurements, except oxidation reduction potential are performed typically by High Performance Liquid Chromatography (HPLC), while, in industrial practice, only ORP can be measured on-line.

Figure 2:
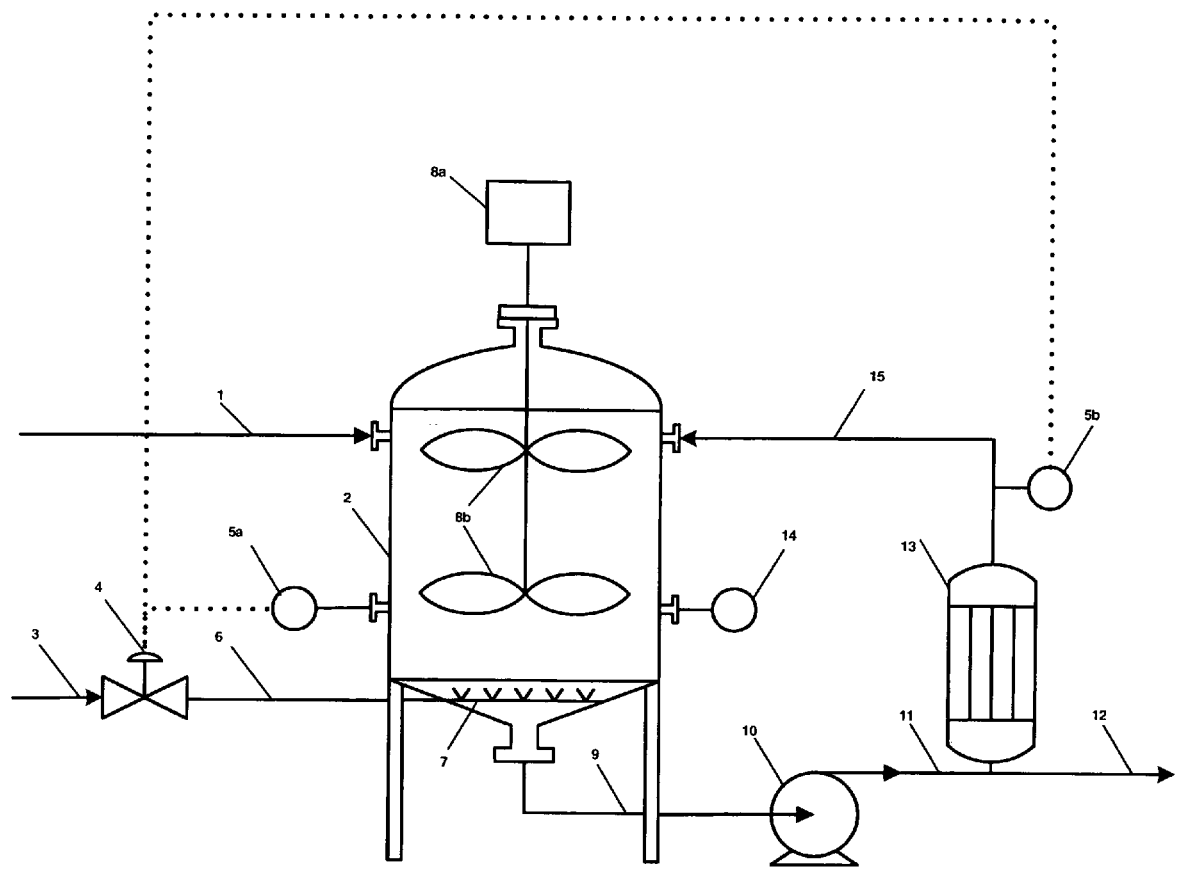
FIG. 2 provides a schematic view of the fermentor used in conjunction with the process of this invention.

FIG. 2 displays air sparging directly into the fermentor (labeled number 2) in order to raise the oxidation reduction potential. Initially, propagated yeast normally enters the top of the fermentor through the pipe numbered 1. As drawn, this feed is shown on the side, but it can enter on the top of the fermentor. Once the yeast enters the fermentor and is filled to a certain level, the yeast solution is closed and the liquefied mash now enters the fermentor, usually in pipe 1, but this feed could enter through a different nozzle location. Upon reaching a certain desired oxidation reduction potential, as measured in either sensor labeled 5A or 5B, high pressure air in pipe numbered 3, enters through the control valve numbered 4. It should be appreciated that an air flow meter in pipe 6 may be placed in this pipe in order to monitor the amount of air flowing to the sparger labeled as part of the equipment numbered 7. Typically, the fermentor contains an agitator with a motor (number 8A) and impellors (number 8B) to thoroughly mix the contents of the fermentor. The fermentor is recirculated through the bottom of the fermentor through pipe numbered 9 and pump 10. During fermentation, all the liquid is sent through pipe numbered 11 and none of the fluid through pipe numbered 12. The shell and tube exchanger numbered 13 cools the fermentation liquor to remove the heat of fermentation. It should be appreciated that although a shell and tube exchanger is shown, a spiral exchanger or plate and frame exchanger could be used. Typically, chilled water is used to maintain the fermentation temperature. The chilled liquid then enters back into the fermentor through pipe 15. Once fermentation is completed, the beer exits through pipe numbered 12, and usually, no beer enters the pipe numbered 11.

Figure 3:
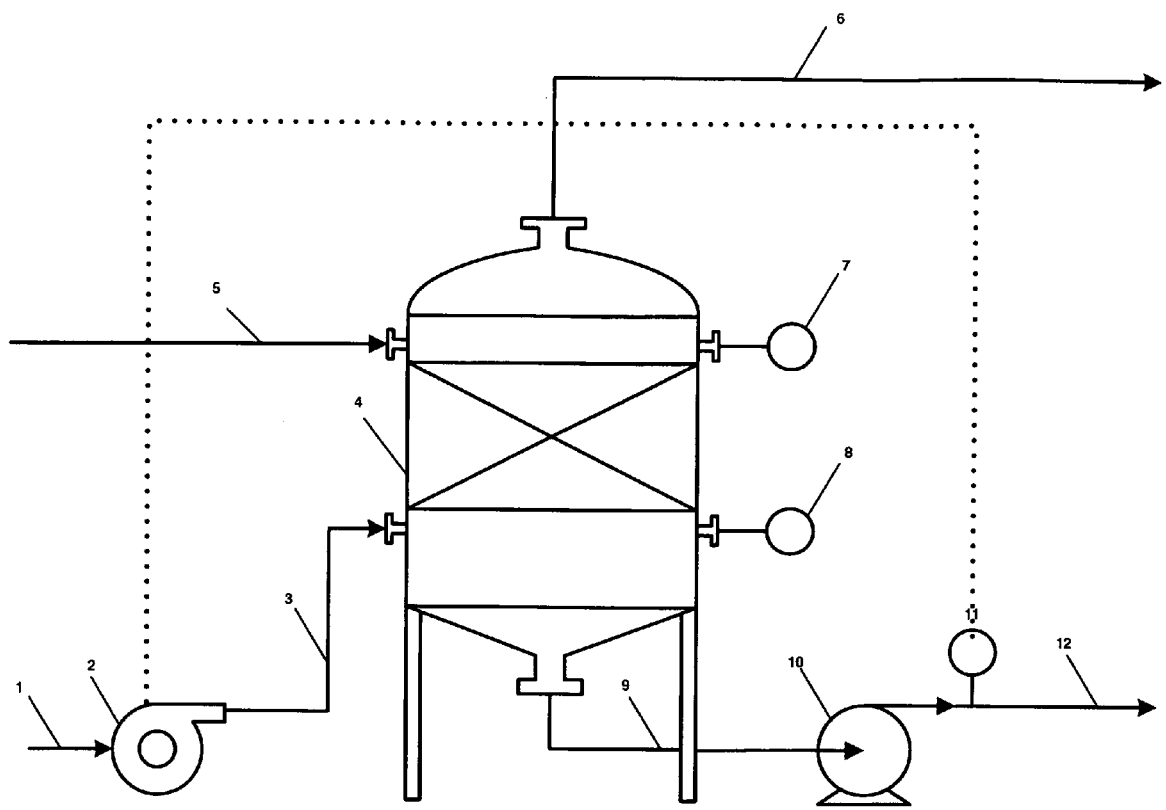
FIG. 3 shows a fermentor feed oxidation vessel, at its various associated operative accessories.

FIG. 3 shows ambient air being admitted to the system through pipe numbered 1 and then discharged by fan numbered 2 into a gas duct numbered 3, which is connected near the bottom of a gas-liquid contacting device, which is labeled number 4. Liquefied corn mash enters near the top at location numbered 5 of the contacting device, which can be an open venturi type contactor or a trayed column or other known contacting device, used in the industry. The air exits the contacting device, through duct numbered 6 and then can be sent to the volatile organic compounds burner, for example. This gas-liquid contactor is properly instrumented with level, temperature or pressure monitors, which are shown by numbers 7 and numbers 8. The aerated liquid exits the contactor through pipe numbered 9 and is delivered to the fermentor via pump labeled 10 through pipeline 12. Oxidation Reduction Potential monitor numbered 11 can be controlled by adjusting either the speed or inlet guide vane of air blower numbered 2.

EMBODIMENTS OF THE INVENTION

One embodiment is to eliminate reductants such as ammonia, urea or sulfur dioxide from entering the corn mash. Ammonia and urea can be replaced with caustic. The increased ethanol sales through reductant elimination is expected to more than offset any increased chemical usage cost. The projected profit increase can be as much as 3 Million for a 25 Million Gallon per year plant. However, there is concern that the replacement of ammonia ions with sodium ions may have an adverse impact on the yeast. Ingledew reports in page 52 of *The Alcohol Textbook* that sodium limitations of 500 ppmw should be placed on the yeast *Saccharomyces Cerevisiae*. Curran and Montville writing in "Bicarbonate inhibition of *Saccharomyces Cerevisiae* and *Hansenula wingei* growth in apple juice" in the International Journal of Food Microbiology in February 1989, pages 1–9 that as much as 5500 ppmw.

Another embodiment is shown in FIG. 2, where air or oxygen is added directly to the fermentor. This approach will require more capital than the substitution of caustic for ammonia or urea. Sparging alleviates the detrimental effect of sodium on the yeast. Additionally, oxidation reduction potential, since it is measured in the fermentor can be controlled to almost any level by simply adjusting the amount of air (oxygen) going to the fermentor. Direct feedback of the redox potential is then accomplished.

An additional benefit is that the yeast propagation tank can be eliminated, since a fully oxidizing environment can be attained in the fermentor. There are two problems encountered with this approach. First, air addition directly into the fermentor will dilute the carbon dioxide leaving the fermentor. In some ethanol plants, the carbon dioxide byproduct is an attractive revenue source. Air dilution may render the carbon dioxide stream unrecoverable. Secondly, air bubbling is not an efficient method of contacting liquid with gas streams. Considerable energy is wasted in this approach.

An alternate method of efficiently contacting air and liquid is through a lower pressure contacting device. As discussed earlier, there are many gas-liquid contacting devices that are practiced by one skilled in the art. Instead of higher pressure air, as shown in FIG. 2, air is supplied via a blower, which can be modulated either by an inlet guide vane or a variable speed drive. These blowers consume a lower amount of energy. As in FIG. 2, the yeast propagation tank can be eliminated. Since the broth is aerated prior to the fermentor, the carbon dioxide product can be recovered, thereby retaining the associated revenues. However, there is a lag between ORP in the fermentor, and the ORP in the feed stream. In addition, the required capital for this invention is considerably more than either two previously mentioned options, since there is additional equipment, instrumentation and controls. Site economics will dictate the most attractive embodiment.

In all cases, the downstream equipment from the fermentors is assumed to be sized for the increased ethanol concentration. Otherwise, there would be a need to debottleneck the distillation and dehydration equipment and possibly the storage tanks to allow the full economic benefit of this invention to be realized.

Variations or modifications to the subject matter of this invention may occur to those skilled in the art upon review of the invention as described herein. Such variations, if within the spirit of this development, are intended to be encompassed within the scope of the invention as defined. The description of the preferred embodiments, specific example set forth, and all as shown in the drawings, are set forth for illustrative purposes only.

I claim:

1. A process for efficiently producing ethanol through application of anaerobic fermentation comprising:
 a. providing a closed vessel having both an inlet and outlet, and at least one feed inlet for introducing of fermentable mash into the vessel;
 b. said fermentable mash having a percentage of ingredients selected from the group including at least one of corn, milo, barley, wheat, oats, sugar cane, and molasses;
 c. said fermentable mash including water in an amount between about 55% to 90% by weight;
 d. adding an enzyme into the mash-water mixture to initiate the enzymatic breakdown of the starch content of the mash;
 e. adding a yeast into the mixture to further initiate the fermentation process;
 f. aerating the fermenting mash in the vessel through the addition of pressurized air or oxygen into the contained mash;
 g. continuing the aeration of the aqueous mash solution in the closed vessel and determining the oxidation-reduction potential of the fermenting mash and maintaining a voltage potential between about −250 millivolts to +50 millivolts to attain the most efficient fermentation of the mash to achieve the maximum ethanol yield.

2. The process of claim 1 wherein the oxidation-reduction potential of the fermentable mash is elevated in ph through reductant substitution by decreasing of ammonia through the addition of a caustic solution.

3. The process of claim 1 wherein the sulfite, bi-sulfite or sulfur dioxide in the mash are oxidized through said addition of air or oxygen to elevate the oxidation-reduction potential of the fermentable mash.

4. The process of claim 1 wherein an oxidant is added to the fermentable mash in order to raise the oxidation-reduction potential of the fermentable mash.

5. The process of claim 4 wherein the oxidant is hydrogen peroxide.

* * * * *